(12) United States Patent
Sesic

(10) Patent No.: US 6,398,786 B1
(45) Date of Patent: Jun. 4, 2002

(54) STRAIN-INDUCING CONICAL SCREW FOR STIMULATING BONE TRANSPLANT GROWTH

(76) Inventor: Nenad Sesic, Prilaz V. Brajkovica 10, HR-10020, Zagreb (HR)

( * ) Notice: Subject to any disclaimer, the term of this patent is extended or adjusted under 35 U.S.C. 154(b) by 0 days.

(21) Appl. No.: 09/719,520

(22) PCT Filed: Oct. 6, 1998

(86) PCT No.: PCT/HR98/00004

§ 371 (c)(1),
(2), (4) Date: Feb. 27, 2001

(87) PCT Pub. No.: WO99/18873

PCT Pub. Date: Apr. 22, 1999

(30) Foreign Application Priority Data

Oct. 9, 1997 (HR) .......................... P970539A
Jun. 17, 1998 (HR) .......................... P980332A

(51) Int. Cl.$^7$ ............................................. A61B 17/56
(52) U.S. Cl. ........................ 606/73; 411/411; 411/415
(58) Field of Search .............................. 606/53, 60, 72, 606/73; 411/263, 411–413, 415, 426, 307

(56) References Cited

U.S. PATENT DOCUMENTS

| 2,382,019 A | * | 8/1945 | Miller | 411/378 |
| 3,799,229 A | | 3/1974 | Johnson | |
| 3,918,345 A | * | 11/1975 | Phipard, Jr. | 411/416 |
| 5,252,016 A | * | 10/1993 | Schmid et al. | 411/386 |
| 5,356,253 A | * | 10/1994 | Whitesell | 411/188 |
| 5,403,136 A | * | 4/1995 | Mathys | 411/310 |
| 5,456,685 A | * | 10/1995 | Huebner | 606/73 |
| 5,562,672 A | * | 10/1996 | Huebner et al. | 606/73 |
| 5,882,162 A | * | 3/1999 | Kaneko | 411/411 |
| 5,964,768 A | * | 10/1999 | Huebner | 606/73 |
| 6,030,162 A | * | 2/2000 | Huebner | 411/413 |
| 6,086,303 A | * | 7/2000 | Fluckiger | 411/399 |

FOREIGN PATENT DOCUMENTS

| DE | 3119583 | 12/1982 |
| EP | 0704281 | 4/1996 |
| EP | 0716832 | 6/1996 |
| WO | 9300518 | 1/1993 |
| WO | 9416636 | 8/1994 |
| WO | 9420040 | 9/1994 |
| WO | 0918356 | 6/1996 |
| WO | 9620650 | 7/1996 |

* cited by examiner

*Primary Examiner*—Jeffrey A. Smith
*Assistant Examiner*—Michael B. Priddy

(57) ABSTRACT

The invention involves a differential and/or conical screw of a variable increasing pitch which is used for the initial mechanical stimulation of a healthy bone, in order to induce a new internal strain and the consequential biological reaction of the bone. The biological reaction results in the formation of a new, young superficial bone, and the process takes between 4 and 8 weeks. The new bone is used as an autologous bone transplant. The transplantation of this new bone into other parts of the body, where such a procedure is indicated, is a new method referred to as adaptive periosteal cambiplasty. The process of the implantation of the screws into the bone is controlled with the use of a special moment key, which provides for the induction of a defined and desired stimulation force, and it also provides for the safety of the method.

8 Claims, 1 Drawing Sheet

STRAIN-INDUCING CONICAL SCREW FOR STIMULATING BONE TRANSPLANT GROWTH

This application is the national phase under 35 U.S.C. §371 of PCT International Application No. PCT/HR98/00004 which has an international filing date of Jun. 17, 1998, which designated the United States of America.

BACKGROUND FIELD OF THE INVENTION

The invention pertains to the area of bone reconstruction in orthopaedic surgery and traumatology and it will find its application in the management of "pseudoarthrosis defects" in which a bone fragment is missing due to a bone defect. The bone fragment must be replaced by a transplant in order to facilitate a successful healing process. Such bone defects are usually consequences of a major trauma (for example gunshot wounds). They are also seen in open fractures for which a surgical procedure is required to remove a destroyed bone fragment, also following infections (osteomyelitis), requiring the removal of bone sequesters, and finally after the removal of bone tumours or cysts. Besides the aforementioned "pseudoarthrosis defect", the area also encompasses the so called "avascular pseudoarthroses" in which there is a lack of viable bone cells in the area of the fracture as a result of bone devascularisation due to a radical surgical procedure, so that the healing process falls to occur (although the bone edges may be in contact). That is why a method of osteoinduction, including autologous bone transplant is also applied for these cases.

DESCRIPTION OF THE PRIOR ART

The purpose of a bone transplant is of two kinds:
1. It represents a medium for the appositional growth of bone cells from the edges of a bone defect. For this reason, and owing to its faster revascularisation, a spongy structure is more suitable than the homogenous one.
2. A transplant should have the local osteoinductive effect, which can only be found in a viable tissue contaning the living bone cells (osteoblast) which generate a new bone by the secretion of osteoid—protein into which calcium hydroxyapatit is deposited, thus forming a mineral, solid inorganic part of the bone.

The basic technical problem is how to obtain a transplant of a highest possible quality (with the highest degree of viability), which will produce strong osteoinduction using the effect of the living transplanted cells (osteoblast cells). In addition the above mentioned transplant, the bone morphogenic protein induction method, using the bone morphogenic protein (BMP) extracted from the ox-bone, is becoming increasingly more popular. Some other methods, involving locally altered growth factors, are currently in the stage of experimental research work. Although none of these cells are the living cells, BMP placed locally into the traumatised area stimulates the growth of the neighbouring cells and induces more intensive bone formation.

In my previous patent application submitted to the State Office for Intellectual Property on Oct. 9, 1997, the reference number P970539A, I presented the static and dynamical method of the mechanical induction of the periosteal reactive bone growth. The former method is the one using conus screws with a self-tapping tip which provides for a much simpler procedure, since its application does not require any subsequent stimulation. It has been found that the optimum result is achieved by a wedge-shaped screw placed at an angle of 7°. However, the width of the upper part of the opening corresponds only to the diameter of initial part of the screw. The latter gradually widens so that the final diameter of the upper part of the screw is over 0.5 mm bigger than the diameter of the its diameter at the entry. Thus, as it keeps penetrating deeper into the bone, the screw behaves as a wedge which overstrains the bone and pushes it laterally. This results in an osseous reaction, induced during the period of 4 to 8 weeks on the surfaces around the screw. These newly ossified surfaces are then removed by a chisel and transferred to the operative field in the area of the bone defect.

The methods for the surgical management of bone defect involve free bone transplants, the Ilizarov method of segment transplantation and microsurgical vascularised bone transplant. Free bone transplants methods are the most numerous, the simplest for application and therefore the most widely used ones. They comprise:

1. Autologous spongioplasty (the recipient's own cancellous bone—red bone marrow) which is widely accepted as the best osteoinduction material since it contains its own viable cells, and is of a spongy structure. It is usually taken from the pelvis (crista iliaca).
2. Corticospongioplasty—besides the internal, spongy part of the bone, this method also uses the external, solid, cortical part of the bone. The cortical part itself is less valuable as an osteoinduction medium, since it contains a low osteoblast count, and by its structure it is a homogenous, solid bone (which becomes dead after the transplantation), so that at a later stage it has to be totally turnovered by new cells from the neighbouring bone tissue. However, its advantage lies in the fact that it has very good mechanical hardness. It is usually taken from the pelvis area or from the medium third of the fibula.
3. Homologous spongioplasty (human cancerous bone taken from a bone bank) is being abandoned (AIDS, hepatitis, reaction to foreign proteins, infection etc.) and is being replaced by the use of artificial osseous tranplants.
4. Transplantation of an artificial bone. This method is gaining in popularity owing to its major advantage which lies in the fact that the transplanted tissue is not the recipient's own bone, which reduces the surgical trauma sustained by the recipient. A shortcoming of this method lies in the fact that these transplants do not contain viable cells, but they serve as a spongy medium for the implantation of the neigbouring cells, so that the healing process is much slower and of a much lower quality than with the application of autologous spongioplasty. This group consists of two types of transplants. The first group are the transplants originating from biological tissue (bovine spongiosis, collagen, collar minerals and so on). The second group is relative to transplants of inorganic origin (hydroxiapatit). Many of these are protected under different names such as Bio-Oss® (Geistlich AG, Switzerland), Osteovit® (B. Braun Melsungen AG), and others.
5. Decortication of Judet (M. E. Mueller and all, Manual of Internal Fixation, Springer-Verlag, Third Ed. 1991,720).
6. BMP (bone morphogenic protein) osteoinduction (OP-1™ striker® BIOTECH).
7. Periosteum transplantation is mentioned only sporadically in literature and it is described in all insignificant number of cases. It is not widely used due to the uncertainty regarding the subsequent bone formation, i.e. due to a much higher degree of efficiency and safety of the previously mentioned methods.
8. Reactive Cambiplasty by means of a conical screw induces periosteal reaction which is then used as an periosteal autologous bone transplant (P970539A).

The second group of operative methods for the surgical management of bone defects consists of the segment transport according to Ilizarov and a microsurgical method involving the transplantation of a vascularised bone transplant. However, these two methods differ significantly from the previously described ones since they do not involve a free bone transplant so no comparison is possible between them.

And finally, it should be pointed out that the method of autologous spongioplasty is until now considered to be the best osteoinduction method. This has been corroborated by many scientific research results. Due to the simplicity of its application, this method is also the most widely used one.

The essence of the invention is based on the scientifically proven fact. First presentation of the Adoptive periosteal cambiplasty method and differential conical screw was a IV European FECAVA/SCIVAC Congress, Bologna, Italy Jun. 18–21 1998. Second presentation was at XXIII World WSAVA Congress, Buenos Aires, Argentina Oct. 5–9 1998. That the recipient's own mechanically induced periosteal reaction on the bone surface after 4 to 8 weeks shows a substantially higher (even twice as high) osteoinduction potential than the recipient's own cancellous bone (red bone marrow).

It should be emphasised at this point that for two reasons this reaction cannot be mistaken for a common periosteal callus which appears in fractures. These reasons are as follows:

1. The reaction occurs as an adjustment to a new strain in the bone, and not as a reaction to a trauma. The induction of growth of new osseous cells (osteoblasts) is a result of turnover resulting from altered, intentionally induced and increased internal strain which occurs in an otherwise healthy bone with an uninterrupted osseous continuity, rather than as a sequeala of a fracture and part of its natural healing process.
2. Histologically, the only tissue present is the bone tissue, whereas the tissue of a fracture callus is mixed with the adjacent callus from the haematoma, the endosteal part and the muscle. We may even come across cartilage fragments. This difference is evident microscopically and may be proven in a number of ways.

The above mentioned method was referred to as "cambiplastica reactiva" in my previous patent application since this name provides for the anatomical definition of the method and thus distinguishes it from periosteal transplantation. Periosteum consists of two layers, the external fibrous layer which contains blood vessels and capillaries, and the internal, cambial layer which contains a very thin layer of the so called osteoprogenitor cells, the antecedents of osteoblasts. By some atoms it contains, this layer does not belong to the periosteum but rather to the bone, which is to a certain extent corroborated by my research. As has been said already, neither the periosteum nor the cambial layer are transplanted. The method consists of the surgically induced mechanical changes to the internal strain which, in turn, induce the reaction within the cambial layer. After 4 to 8 weeks, the quantity of the reaction, i.e. of the newly-formed bone, is sufficient for transplantation into another part of the body where there is a lack of bone tissue or where osteoinduction is required (for example atrophic pseuodarthrosis or prolonged osseous healing, etc.).

This delayed transplantation of the osseous tissue generated by previous mechanical stimulation is a novelty and the essence of the invention. Therefrom the name "reactive Cambiplasty" rather than only cambiplasty. Cambiplasty as such does not exist. If it did, it would fall under the category of periosteum transplantation. In this procedure, the periosteum chiselled from the surface of the bone would contain a part of the cambial layer. However, in this stage (without prior mechanical stimulation), this is a microscopical layer of the soft tissue, rather than of a solid bone (of a slightly spongy consistence) as a reaction in the "reactive cambiplasty". Moreover, it has already been said that the method of periosteal transplantation is not widely accepted due to the uncertainty of its results.

My subsequent scientific research resulted in some new notions and, consequntly, in the change of the definition of the previously described cambial reaction. This, in turn, has resulted in the change of the method's name, which is now called "adaptive periosteal cambiplasty". The term "adaptive" refers to the adaptation of the bone to a new strain, and is not restricted to the description of a periosteal reaction. The term periosteal closely describes the area involved, and cambiplasty refers to the part which is being transplanted. The essence of this invention is the improved mechanical action of the differential conical screw (FIG. 3) as opposed to the effect of the conical screw described in my previous patent application, reference No. P970539A. The screw is not placed in the previously threaded conical hole, but rather into a straight hole in the bone, most commonly through a single corticalis in the area of the tibial diaphysis. In this hole a thread of the same pitch and diameter as the lower, cylindrical part of the screw, is made by a thread cutting tap. The pitches of the thread may be between 0.3 and 2 mm. During the twisting of the differential conical screw into the bone, its conical shape induces distractional radial forces around the screw in the bone. These forces tend to be stronger in the surface parts of the bone owing to the conical shape of the screw. This difference in the stress—strain distribution of the radial forces in the surface and deep layers of the bone constitutes the main difference between the effect of this differential conical screw and the effect of the simple conical screw described in my previous application. Conical (wedge) angle of the screw may vary between 1° and 10°. Optimal angle is about 7° or halfangle of 3.5° (FIG. 3).

The second difference is contained in the term "differential", which is a word referring to the function of the screw and implying the kinematics of the twisting of this screw into the hole in the bone. Besides the conical shape, this screw also features a variable thread pitch in its cone part, which increases gradually from its lower, cylindrical part, to its head. This increase is continuous and incremental at each thread, and may vary between 0.01 and 0.1 mm per thread. This variability of the screw pitch is typical of this particular screw shape resulting in the above mentioned differential function, which is made possible by the differences in thread pitches, which are shorter and prethreaded in the osseous part. For this reason, the twisting of such a screw into the cylindrical hole in the bone, which features the prethreaded screw pitches, corresponding to the pitches in the cylindrical part of the screw, starts as a normal procedure, but later on, after 2 to 5 threads, as the screw penetrates deeper into the bone, it induces distraction forces and sress—strain distributions which are axial to the axis of the screw. This bone extension provides for additional stimulation and is conducive to the above mentioned adaptation reaction appearing on the bone surface, which in turn results in the generation of the future autologous bone transplant. The screws need be produced from common implant materials—stainless steel ISO 5832/6 or 5832/IV or 5832-8 or from a titanium alloy for ISO 5832-3.

REALISATION METHODS

Figure 3:
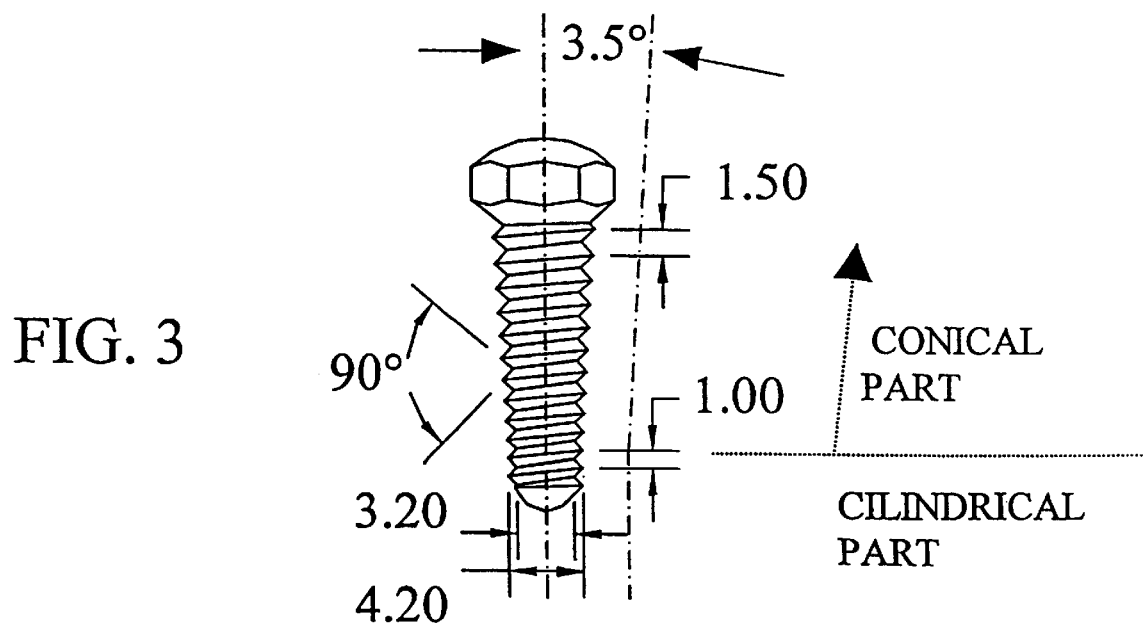
FIG. 3 shows a planar view of the differential conical screw according to the preferred embodiment of the invention

In distinction to the previous, already mentioned patent application, reference number P970539A, the realisation of the procedure referred to as adaptive periosteal cambiplasty requires only a static approach improved by an additional stimulation force. This stress—strain distribution is a result of the twisting of the differential (and/or) conical screw (FIG. 3), and it is radial and axial to the axis of the screw itself.

Figure 2:
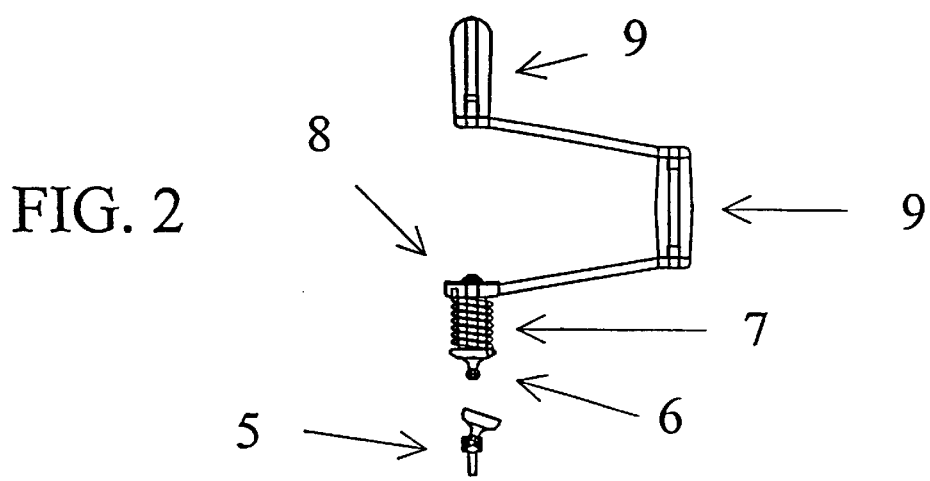
FIG. 2 shows a torque wrench for connection with the differential conical screw of the present invention.

The twisting of this conical screw into the bone, is facilitated by a specially designed moment key (FIG. 2) which provides for a precise control and thus for the good prediction of the level of the stimulation force within the bone, and prevents a possible bone fracture caused by the thus induced forces. To further facilitate the application, an adapter has been mounted between the torque wrench and and the conical screw. Owing to the round sextant of the terminal part of the torque wrench, the adapter has the effect of a universal joint. Its application reduces the induction of a twisting force within the screw itself, and facilitates the procedure.

Figure 1:
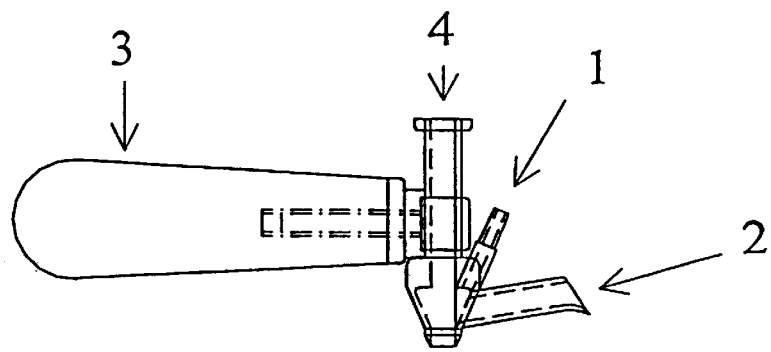
FIG. 1 shows a drill guide with a lateral inflow pipe and outflow pipe.

During the drilling of the hole in the bone, we use the drill guide (FIG. 1) with the lateral inflow and outflow of water through which a saline solution is injected during the drilling procedure. This has two positive effects. The first one is the reduction of temperature, which is a result of the drilling, and which may damage the bone tissue adjacent to the hole. The second positive effect lies in the fact that the saline washes away bone detritus, thus improving the quality and the precision of the drilling

APPLICATION OF THE INVENTION

The invention is applied in the same way as the previous one described in the patent application no P970539A. In cases of a bone defect (trauma, bone cysts, the sequela of previous surgical procedures, etc.) a stimulation procedure is undertaken 4 to 8 weeks prior to the scheduled main surgical procedure. During the main procedure, the osseous tissue resulting from the reaction induced by the stimulation of the cambium layer, is chiselled off (a standard procedure of for obtaining autologous bone transplant) and transferred into such part of body where it needs to be implanted and where it will start an osteoinduction process.

The invention is applied by a simple use of the above mentioned differential (and/or) conical screw which is placed into the bone by means of a few additional instruments. The screw is applied precutaneously, most commonly into the tibial dyaphisis, where the bone is found very close to the skin. The first additional instrument is a drill guide (FIG. 1) with the lateral inflow pipe (1—FIG. 1) and outflow pipe (2—FIG. 1) for the irrigation During the drilling procedure, this is used for the injection of a saline solution The drill guide possess a handle (3—FIG. 1) and a drill sleeve tube (4—FIG. 1). The hole in the bone is threaded by means of a tap of the same pitch and diameter as in the cylindrical part of the differential (and/or) conical screw which may vary between 2 and 8 mm in diameter. The connection between the moment key—torque wrench (FIG. 2) and the differential conical screw is established by an adapter (5—FIG. 2). The adapter has a hexagonal wrench for the screw at one end and a socket wrench for the rounded sextant on the lower end of the torque wrench (6—FIG. 2). Head of the screw may be in sextant form (as in FIG. 3), may possess rounded head with adjoining flat side peripheral surfaces for engagement with a hexagonal socket of may be in the form of a joint, or without the head and so directly connected to the screwdriver via hexagonal socket. Next step is the twisting of the differential conical screw using the moment key. The process results in the desired torsion force and bone stimulation. The torque wrench conveys the force via a torsion spring (7—FIG. 2) in its lower part and the force is expressed as an angular shift on the scale (8—FIG. 2). The moment key is set in motion via two handles (9—FIG. 2). It may be made also in the form of one handle like simple lever or wrench. The values of force momentums are obtained experimentally by measuring, they are expressed in a tabular form and they are relative to the bone thickness, length etc.

What is claimed is:

1. A differential conical screw, comprising a cylindrical lower portion and a conical upper portion, each of said lower portion and said upper portion comprising screw threads, wherein said cylindrical lower portion extends over a distance of between two to five screw threads, and wherein said conical upper portion comprises a screw thread which is of increasing pitch.

2. A differential conical screw according to claim 1, wherein said increasing pitch is a constantly increasing pitch.

3. A differential conical screw according to claim 1, wherein said increasing pitch is a variable thread pitch.

4. A differential conical screw according to any one of claims 1 to 3, wherein said screw comprises a sextant-shaped head.

5. A differential conical screw according to any one of claims 1 to 3, wherein said screw includes a rounded head with adjoining flat side peripheral surfaces for engagement with a hexagonal socket.

6. A differential conical screw according to any one of claims 1 to 3, wherein said screw comprises a Phillips head.

7. A differential conical screw according to any one of claims 1 to 3, wherein said screw is formed without a head, for direct connection to a screwdriver via a hexagonal socket.

8. A differential conical screw according to any one of claims 1 to 3, wherein said screw is constructed from stainless steel bone implant material ISO 5832/6 or 5832/IV or 5832-8 or from a titanium alloy material for implants ISO 5832-3.

* * * * *

UNITED STATES PATENT AND TRADEMARK OFFICE
CERTIFICATE OF CORRECTION

PATENT NO.    : 6,398,786 B1
DATED         : June 4, 2002
INVENTOR(S)   : Nenad Sesic It is certified that error appears in the above-identified patent and that said Letters Patent is hereby corrected as shown below:

<u>Title page,</u>
Item [30], Foreign Application Priority Data, delete
"Oct. 9, 1997    (HR) ……………….P970539A"

Signed and Sealed this

Fifteenth Day of October, 2002

*Attest:*

*Attesting Officer*

JAMES E. ROGAN
*Director of the United States Patent and Trademark Office*